(12) United States Patent
Funk et al.

(10) Patent No.: US 7,307,521 B2
(45) Date of Patent: Dec. 11, 2007

(54) SECURE METHOD AND APPARATUS FOR RETRIEVING NETWORK NODE IDENTIFIER IN WIRELESS NETWORKS

(75) Inventors: Karsten Funk, Stuttgart (DE); Bhaskar Srinivasan, Belmont, CA (US)

(73) Assignee: Robert Bosch GmbH, Stuttgart (DE)

( * ) Notice: Subject to any disclaimer, the term of this patent is extended or adjusted under 35 U.S.C. 154(b) by 215 days.

(21) Appl. No.: 11/077,631

(22) Filed: Mar. 10, 2005

(65) Prior Publication Data

US 2006/0208880 A1    Sep. 21, 2006

(51) Int. Cl.
*G08B 1/08* (2006.01)
*H04Q 7/00* (2006.01)

(52) U.S. Cl. .................... 340/539.1; 73/146.4
(58) Field of Classification Search ............. 340/539.1, 340/514, 628, 505, 933, 941, 539.13, 448, 340/447, 426.35; 73/146.4, 146.5
See application file for complete search history.

(56) References Cited

U.S. PATENT DOCUMENTS

| | | | |
|---|---|---|---|
| 4,308,520 A * | 12/1981 | Darlington ................. 73/146.5 |
| 5,335,246 A | 8/1994 | Yokev et al. |
| 5,771,438 A | 6/1998 | Palermo et al. |
| 5,809,059 A | 9/1998 | Souissi et al. |
| 5,873,070 A * | 2/1999 | Bunte et al. ................... 705/28 |
| 6,353,406 B1 * | 3/2002 | Lanzl et al. ................. 342/118 |
| 6,374,079 B1 | 4/2002 | Hsu |
| 6,424,820 B1 * | 7/2002 | Burdick et al. ............ 455/41.1 |
| 6,459,882 B1 | 10/2002 | Palermo et al. |
| 6,529,127 B2 | 3/2003 | Townsend et al. |
| 6,571,617 B2 * | 6/2003 | Van Niekerk et al. ......... 73/146 |
| 6,643,278 B1 | 11/2003 | Panasik et al. |
| 6,838,988 B2 * | 1/2005 | Lennartz et al. ........ 340/539.26 |
| 6,906,624 B2 * | 6/2005 | McClelland et al. ......... 340/442 |
| 7,040,139 B2 * | 5/2006 | Sunshine ..................... 73/23.2 |
| 7,088,226 B2 * | 8/2006 | McClelland et al. ......... 340/442 |
| 7,089,099 B2 * | 8/2006 | Shostak et al. ............... 701/32 |
| 2002/0132585 A1 | 9/2002 | Palermo et al. |
| 2003/0020595 A1 | 1/2003 | Wacyk |
| 2004/0003073 A1 | 1/2004 | Krzyzanowski et al. |
| 2004/0032226 A1 | 2/2004 | Lys |

OTHER PUBLICATIONS

International Search Report for PCT/US2006/005124, Date of Completion Jul. 13, 2006.

* cited by examiner

*Primary Examiner*—John Tweel, Jr.
(74) *Attorney, Agent, or Firm*—Kenyon & Kenyon LLP

(57) ABSTRACT

A sensor node arrangement in a wireless network, includes a sensor to sense information, an RF transceiver to communicate the information to at least one element of the wireless network, and a coil to establish a secondary communications channel with a handheld device via inductive coupling, the secondary communications channel used, for example, to receive, during installation of the sensor node arrangement, a node identifier of the sensor node arrangement.

20 Claims, 6 Drawing Sheets

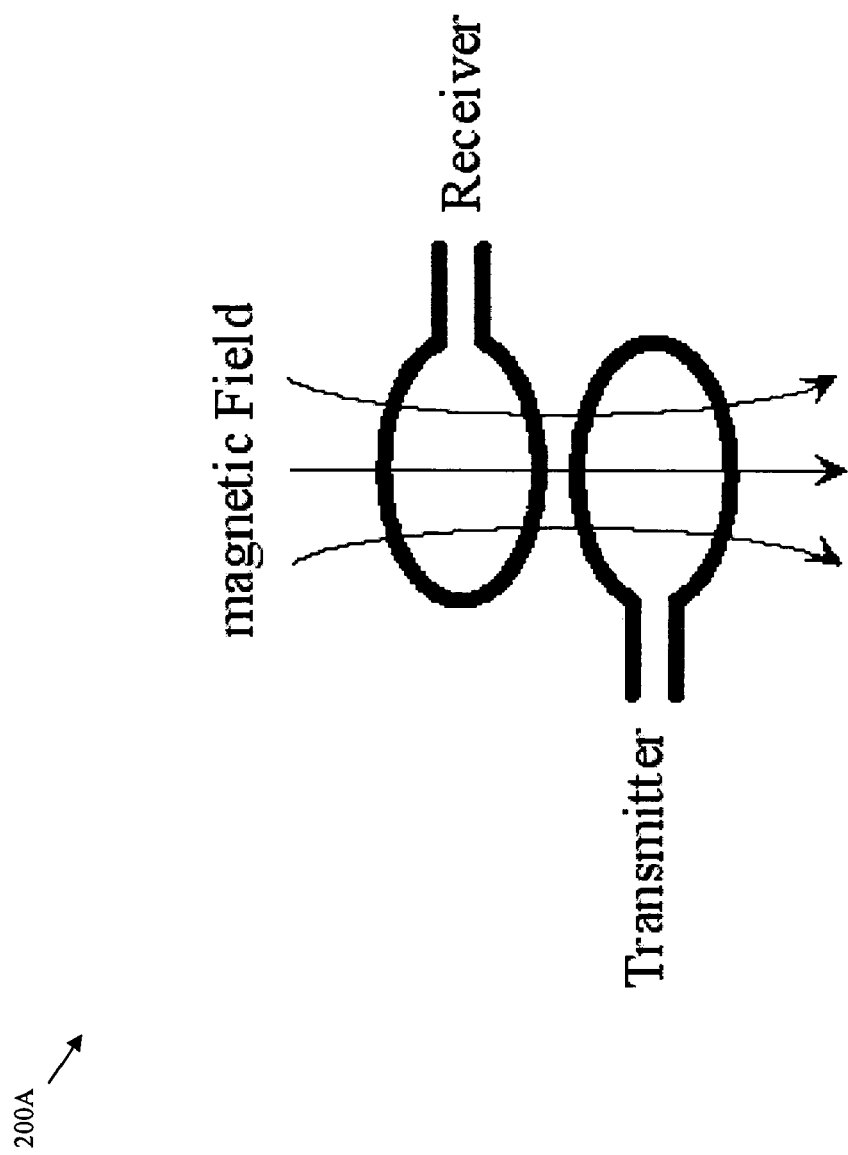

SECURE METHOD AND APPARATUS FOR RETRIEVING NETWORK NODE IDENTIFIER IN WIRELESS NETWORKS

FIELD OF THE INVENTION

The present invention relates to a secure method and apparatus for retrieving a network identifier in wireless networks.

BACKGROUND INFORMATION

Security systems may include several sensors, such as, for example, fire alarm sensors, smoke detectors, movement sensors, glass break sensors, gate/door/window sensors, etc., which may be connected to a central base station by wires. Alternatively, the connecting wires may be replaced by a wireless communication arrangement, where each sensor is arranged as a node in a wireless communication system. Accordingly, installation costs may be reduced and certain security aspects may be enhanced.

Installation errors may occur in wireless networks due to the coordination and correlation of sensors in the system itself. In particular, it may be difficult during installation to know which sensor is (wired or wirelessly) connected to which port or which sensor has which sensor ID. While in wired systems this may be solved by physically checking the wires, in wireless systems it is different, since wireless communication channels cannot be switched off separately. If the system sends an identification request to one sensor that is mounted, for example, in office 'A', and a similar sensor is mounted in office 'B' and within (wireless) reach of the base station (i.e. its coverage area), there may be no way to find out if the sensor in office 'A' or 'B' answers this request. If due to installation errors the sensor assigned to office 'A' is mistakenly installed in office 'B' and vice versa, the system may be unable to recognize the mistake and consequently the system may be left potentially vulnerable to failure.

Every sensor and for that matter every wireless sensor node may have a unique identifier, which is part of the sensor node firmware or may even be, at least partially, hardware defined. In any case, the unique identifier, or at least parts thereof, should be accessible for the node software in order to authenticate the node when exchanging messages with the sensor network.

One way to make this identifier uniquely known to the installer is to attach a label with the identifier on the outside of the sensor case. However, there is a chance that labels may be mixed up or are simply wrong.

SUMMARY OF THE INVENTION

According to an exemplary embodiment and/or exemplary method of the present invention, the sensor node identifier is accessed electrically and communicated to a device the installer uses to record sensor type, sensor node location, assigned identifier, etc., so that a more secure communication scheme may be achieved.

According to an exemplary embodiment and/or exemplary method of the present invention, the installer may use a handheld device during installation, which is comparable to a personal digital assistant, to advise the installer on where to install a particular sensor and to record the sensor identifier from a checklist accessible via the handheld device.

According to an exemplary embodiment and/or exemplary method of the present invention, the handheld device may include a location awareness feature to determine a geographical location within the building so that the handheld device may prompt at any predefined spot which sensor node needs to be installed.

According to an exemplary embodiment and/or exemplary method of the present invention, once the sensor is installed, the handheld device may prompt the installer to record the sensor node identifier by bringing the handheld device in close distance to the sensor node and pointing the handheld device towards a marked spot on the sensor node. The actual wireless communication between the handheld and the sensor node may be realized, for example, by inductive coupling between a coil in the handheld and a coil in the sensor node. In this regard, inductive coupling may be desirable since it is directional and the magnetic field depreciates rapidly with distance. Accordingly, the use of inductive coupling may provide a well-pointed and well-defined identifier recording and at the same time making it nearly impossible for an eavesdropper to intercept the communication signal.

According to an exemplary embodiment and/or exemplary method of the present invention, the inductive coupling component in a sensor node may be realized with only very few additional components. For example, the inductive coupling component may consist of a coil attached to an input/output port of the sensor node micro-controller.

According to an exemplary embodiment and/or exemplary method of the present invention, the transceiver within the sensor node may be configured so that it acts as a passive or active component and thereby draws virtually no power from the sensor node but instead is being powered via inductive coupling from the handheld. Accordingly, the communication may be energy efficient.

According to an exemplary embodiment and/or exemplary method of the present invention, encryption techniques may be used to ensure secure communications between the sensor node arrangement and the handheld device.

An exemplary embodiment and/or exemplary method of the present invention is directed to a sensor node arrangement in a wireless network, which includes a sensor to sense information, an RF transceiver to communicate the information to at least one element of the wireless network, and a coil to establish a secondary communications channel with a handheld device via inductive coupling.

Another exemplary embodiment and/or exemplary method of the present invention is directed to a handheld device for communicating with a sensor node arrangement in a wireless network, which includes a coil to communicate with the sensor node arrangement via inductive coupling.

Yet another exemplary embodiment and/or exemplary method of the present invention is directed to a sensor node network, which includes a network hub, and a sensor node arrangement including a sensor to sense information, an RF transceiver to communicate the information to the network hub, and a coil to establish a secondary communications channel with a handheld device via inductive coupling.

Still another exemplary embodiment and/or exemplary method of the present invention is directed to a method of installing a sensor node arrangement in a wireless network, which includes providing the sensor node arrangement with a coil to communicate with a handheld device via inductive coupling, mounting the sensor node arrangement, bringing the handheld device in close proximity to the sensor node arrangement to allow the inductive coupling to occur, and initiating a communication between the sensor node arrangement and the handheld device via the inductive coupling.

BRIEF DESCRIPTION OF THE DRAWINGS

FIG. 2A shows an exemplary display of inductive coupling principles for a transmitter coil and a receiver coil, in which the coils are arranged in-line with respect to each other.

DETAILED DESCRIPTION

Figure 1:
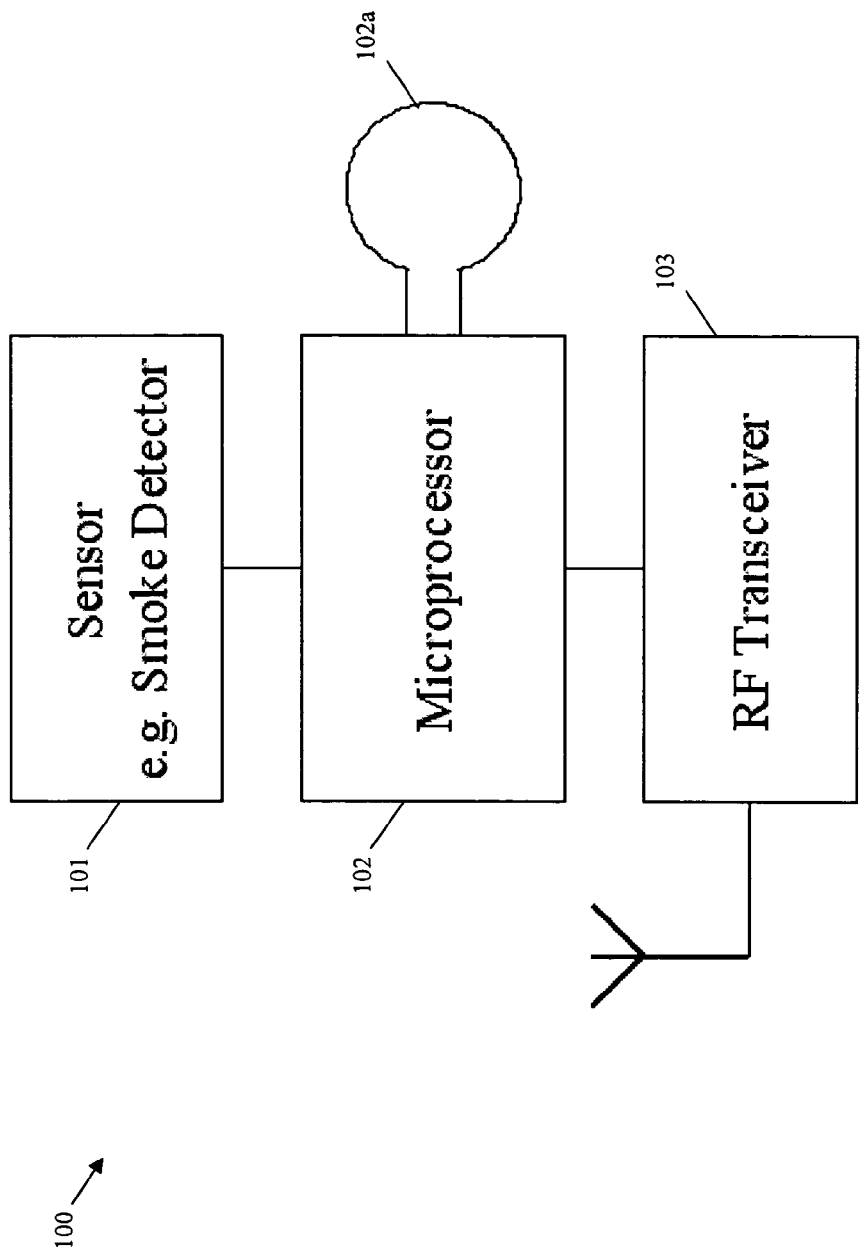
FIG. 1 shows an exemplary sensor node arrangement.

FIG. 1 shows an exemplary sensor node arrangement 100, which includes a sensor device 101, a microprocessor 102, and a RF transceiver 103. The sensor device 101 may include, for example, a smoke detector, a motion sensor, a temperature sensor, a light sensor, etc. The microprocessor 102 may include, for example, an inductive coupler 102a. The RF transceiver 103 may provide, for example, access to network communications during normal operation.

The sensor node arrangement 100 may be part of a sensor node network, installed, for example, in a building, group of buildings, or a campus.

FIG. 2A shows an exemplary display 200A of inductive coupling principles for a transmitter coil 201 and a receiver coil 202, in which the coils are arranged in-line with respect to each other.

Figure 2B:
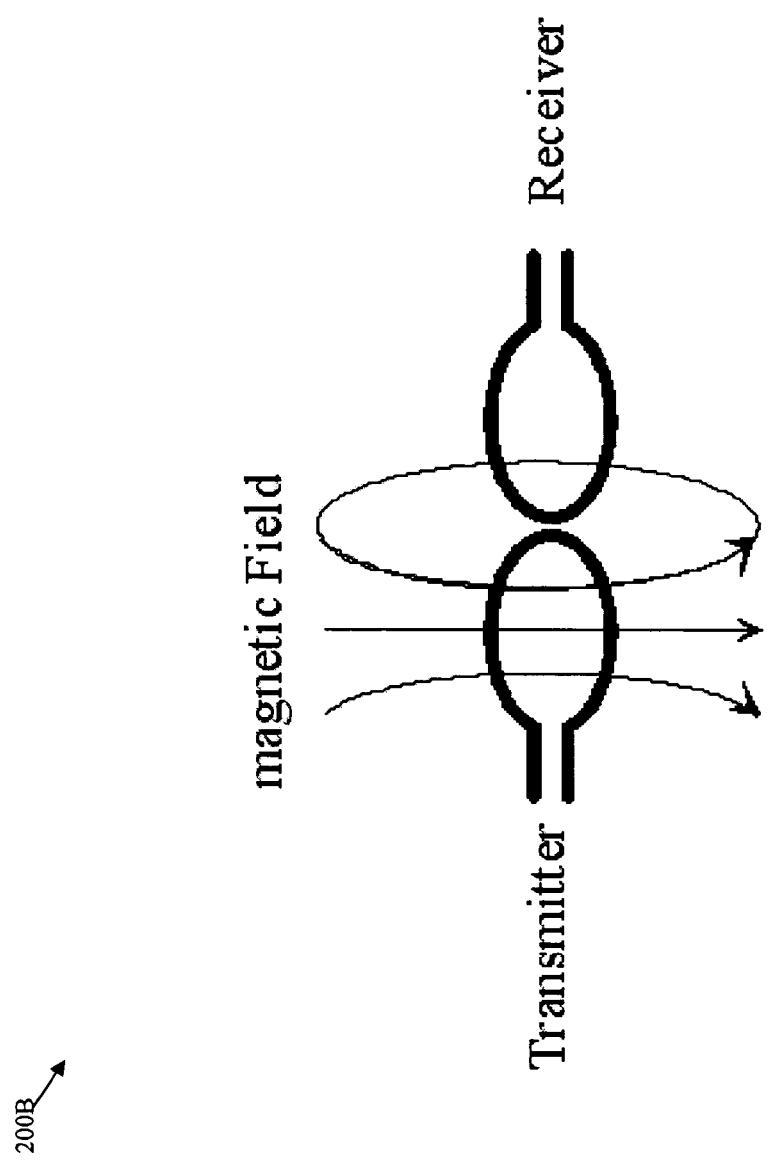
FIG. 2B shows an exemplary display of inductive coupling principles for a transmitter coil and a receiver coil, in which the coils are arranged in parallel with respect to each other.

FIG. 2B shows an exemplary display 200B of inductive coupling principles for a transmitter coil 201 and a receiver coil 202, in which the coils are arranged in parallel with respect to each other.

Figure 3:
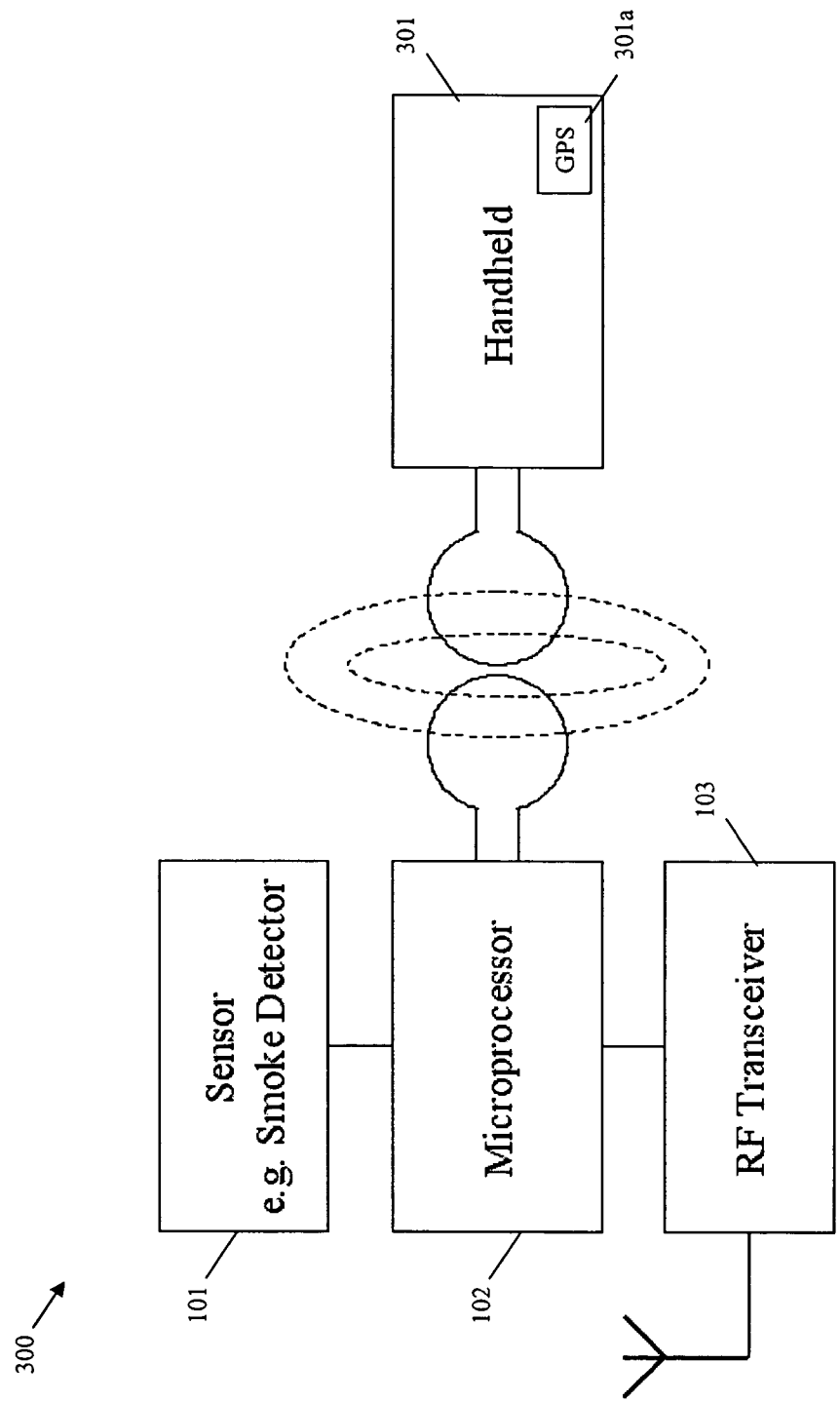
FIG. 3 shows an exemplary interaction between the exemplary sensor node arrangement of FIG. 1 and a handheld device, in which the exemplary interaction occurs via inductive coupling.

FIG. 3 shows an exemplary interaction 300 between the sensor node arrangement 100 of FIG. 1 and a handheld device 301, in which the exemplary interaction 300 occurs via inductive coupling. In this regard, the exemplary sensor node arrangement 100 may communicate a node identifier (ID) and/or other required data to the handheld device 301. The node identifier (ID) may be a unique identifier, which is used, for example, to authenticate the sensor node arrangement when exchanging messages with other elements of the sensor node network. The node identifier may be part of the sensor node firmware or may, at least partially, be hardware or software-defined (e.g., a Radio Frequency Identifier (RFID), Medium Access Address (MAC), or other unique network node identifier). The other required data may be sensitive data and may include, for example, configuration data.

Use of inductive coupling during the installation process, or at other critical times, may provide enhanced security since the communication between the sensor node arrangement 100 and the handheld device 301 during this critical time is effectively localized to a small fixed distance surrounding the sensor node arrangement 100. In particular, unlike RF communications, an inductive coupling signal degrades more rapidly with increased distance so that the potential for eavesdropping is reduced. For example, a potential eavesdropper located outside a building in which the sensor node arrangement is installed may find it nearly impossible to intercept the inductive coupling signal.

The handheld device 301 may include, for example, a global position system (GPS) receiver 301a, or other location-based device, to provide geographic related information. In particular, the handheld device 301 may use the GPS receiver 301a to help pinpoint a particular geographic location of the sensor node arrangement 100, which may be useful for maintaining an accurate fingerprint of an entire sensor node network.

Figure 4:
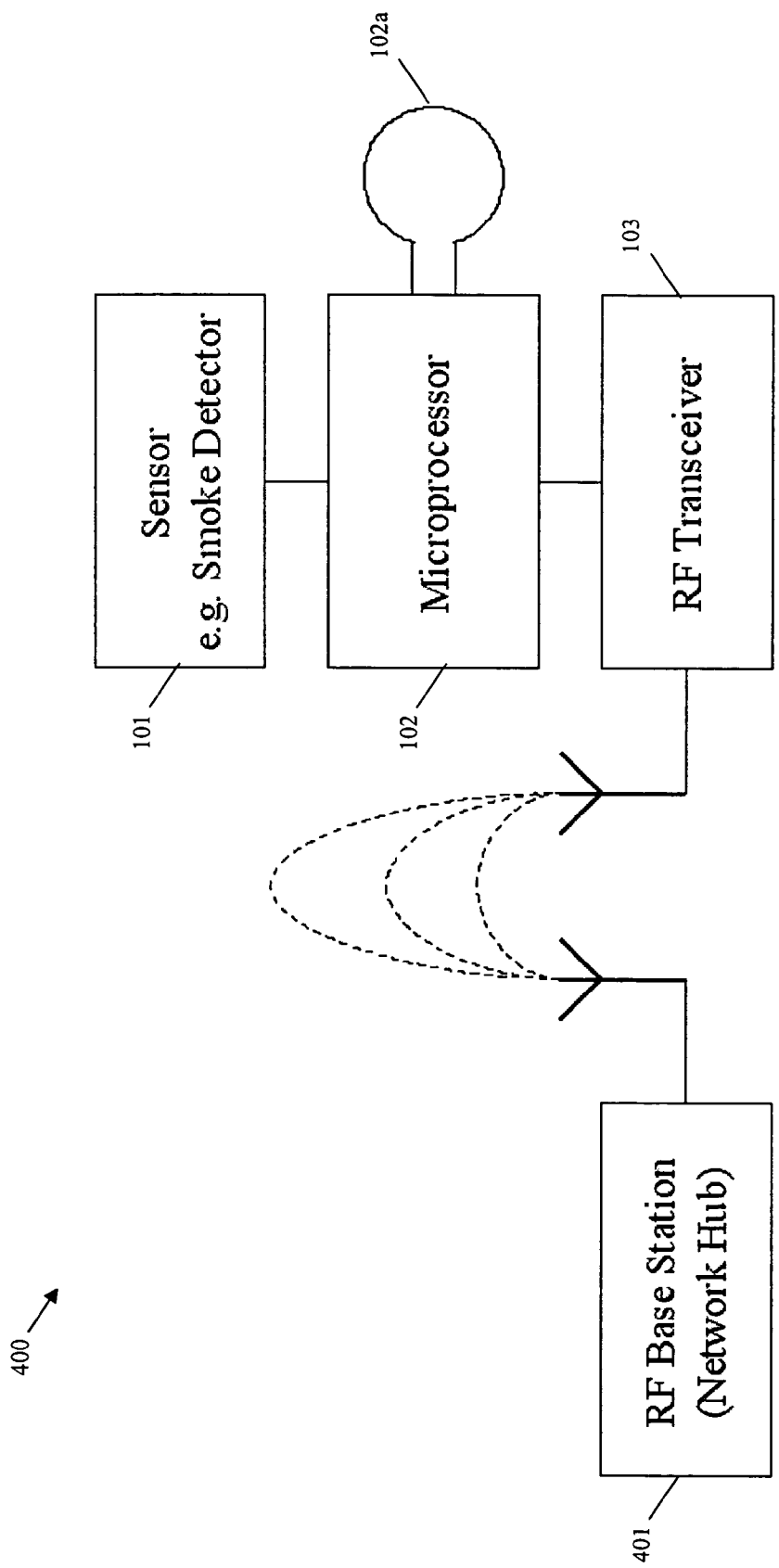
FIG. 4 shows an exemplary interaction between the exemplary sensor node arrangement of FIG. 1 and a base station during normal network operation, in which the exemplary interaction occurs via RF signaling.

FIG. 4 shows the exemplary sensor node arrangement 100 of FIG. 1 communicating with a base station 401 during normal network operation via RF signaling. In this regard, it is noted that the conductive coupler 102a does not draw any power during normal network operation. Moreover, the separate and distinct communications channels provided for installation and for normal operation of the sensor node arrangement may render the installation process less vulnerable to eavesdropping.

Figure 5:
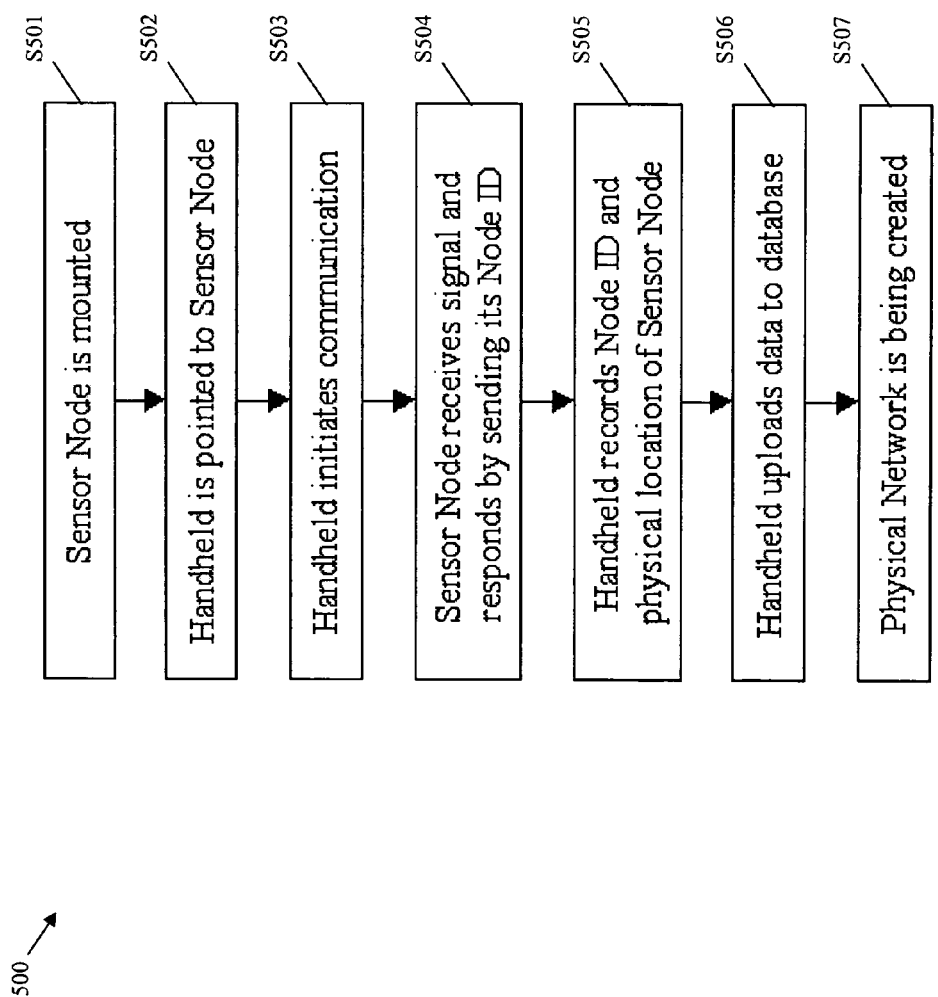
FIG. 5 shows an exemplary method to install the exemplary sensor node arrangement 100 of FIG. 1.

FIG. 5 shows an exemplary method 500 to install the sensor node arrangement 100 of FIG. 1. The exemplary method 500 starts by mounting the sensor node arrangement 100 and continues until the network is created. Each sensor node may be uniquely addressed since its ID as well as geographical location is known.

In step S501, the sensor node arrangement 100 is mounted. In this regard, the sensor node arrangement 100 may be physically secured in a suitable location and in a suitable manner so that sensor node arrangement 100 may operate for its intended purpose. For example, if the sensor node arrangement 100 is intended to sense the motion of an intruder, the sensor node arrangement 100 may be secured to a wall in a main hallway of a building.

In step S502, the handheld device 301 is brought within close proximity of the sensor node arrangement 100 so that the handheld device 301 may interact with the sensor node arrangement via inductive coupling. In this regard, it may be required that the handheld device 301 be pointed towards the sensor node arrangement 100.

In step S503, the handheld device 301 initiates a communication with the sensor node arrangement 100. In this regard, the communication may involve one or more communications protocols, which may be proprietary or conform to an industry standard. A proprietary communication protocol may provide a more secure interface between the handheld device 301 and the sensor node arrangement 100.

In step S504, the sensor node arrangement 100 receives a signal and responds by sending its node ID. Alternatively, or in addition, the sensor node arrangement 100 may respond with other sensitive data, such as, for example, configuration data and/or data related to the capabilities or features of the sensor node arrangement 100.

In step S505, the handheld device 301 records the node ID and physical location of the sensor node arrangement 100. In this regard, the handheld device 301 may include or make use of a located-based service, such as, for example, GPS. Alternatively, the handheld device 301 may simply provide a user interface so that the user may input the physical location.

In step S506, the handheld device 301 uploads data to a database. In this regard, the data may include, for example, the node ID and physical location of the sensor node arrangement 100. The database may include, for example, information regarding the sensor node arrangement 100 not readily available during the installation procedure.

In step S507, a physical network is created. In this regard, the information provided to the database via the handheld device 301 may be used to introduce and/or active the sensor node arrangement 100 within a network of multiple elements, which includes, for example, other sensor node arrangements.

While the exemplary embodiments and methods of the present invention has been described, various modifications and changes may be made thereunto without departing from the proper scope of the present invention of the claimable subject matter.

What is claimed is:

1. A sensor node arrangement in a wireless network, comprising:
   a sensor to sense information;
   an RF transceiver to communicate the information to at least one element of the wireless network; and
   a coil to establish a secondary communications channel with a handheld device via inductive coupling.

2. The sensor node arrangement of claim 1, wherein the secondary communications channel is configured to communicate a node identifier of the sensor node arrangement.

3. The sensor node arrangement of claim 1, further comprising:
   a microprocessor having a printed circuit board, wherein the coil is arranged on the printed circuit board.

4. The sensor node arrangement of claim 3, wherein the microprocessor includes an analog-to-digital/digital-to-analog converter, which is connected to the coil.

5. The sensor node arrangement of claim 3, wherein the coil is configured as a copper line on the printed circuit board.

6. A handheld device for communicating on a secondary communications channel established with a coil of a sensor node arrangement in a wireless network, comprising:
   a coil to receive, via inductive coupling, a communication transmitted on the secondary communications channel established with the coil of the sensor node arrangement.

7. The handheld device of claim 6, wherein the coil is configured to receive a node identifier of the sensor node arrangement.

8. The handheld device of claim 6, wherein the handheld device includes a location-based service arrangement.

9. The handheld device of claim 8, wherein the location-based service arrangement includes a GPS.

10. A sensor node network, comprising:
    a network hub; and
    a sensor node arrangement including a sensor to sense information, an RF transceiver to communicate the information to the network hub, and a coil to establish a secondary communications channel with a handheld device via inductive coupling.

11. A method of installing a sensor node arrangement in a wireless network, comprising:
    providing the sensor node arrangement with a coil to establish a secondary communications channel with a handheld device via inductive coupling;
    mounting the sensor node arrangement;
    bringing the handheld device in close proximity to the sensor node arrangement to allow the inductive coupling to occur; and
    initiating a communication on the secondary communications channel established between a coil of the sensor node arrangement and a coil of the handheld device via the inductive coupling.

12. The method of claim 11, further comprising:
    transferring data from the sensor node arrangement to the handheld device;
    uploading the data from the handheld device to a database; and
    one of creating and updating the wireless network.

13. The method of claim 11, wherein the data includes a node identifier of the sensor node arrangement.

14. The method of claim 11, further comprising:
    recording a physical location of the sensor node arrangement; and
    uploading the physical location of the sensor node arrangement to the database.

15. The method of claim 14, wherein the physical location is recorded using a located-based service.

16. The handheld device of claim 6, wherein the communication transmitted on the secondary communications channel is encrypted.

17. The handheld device of claim 6, wherein the communication transmitted on the secondary communications channel includes initialization data required for initializing the wireless network.

18. The method of claim 11, further comprising:
    transmitting data from the sensor node arrangement to the handheld device via inductive coupling;
    uploading the data from the handheld device to a network hub; and
    storing the uploaded data in a database.

19. The method of claim 18, further comprising:
    initializing the wireless network using the uploaded data.

20. The method of claim 18, further comprising:
    distributing the uploaded data to at least one element of the wireless network.

* * * * *